(12) United States Patent
Betz et al.

(10) Patent No.: US 9,393,116 B2
(45) Date of Patent: Jul. 19, 2016

(54) OSTEOIMPLANTS AND METHODS FOR THEIR MANUFACTURE

(75) Inventors: Randal R. Betz, Ocean City, NJ (US);
Scott D. Boden, Atlanta, GA (US);
Christine Clark, Howell, NJ (US);
Nanette Forsyth, Bayville, NJ (US);
John W. Morris, Beachwood, NJ (US);
Kathy Traianedes, Melvern East VIC (AU)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/618,599

(22) Filed: Sep. 14, 2012

(65) Prior Publication Data

US 2013/0013071 A1    Jan. 10, 2013

Related U.S. Application Data

(63) Continuation of application No. 11/489,262, filed on Jul. 19, 2006, now Pat. No. 8,268,008, which is a continuation of application No. 11/297,735, filed on Dec. 8, 2005, now abandoned, which is a continuation of application No. PCT/US2004/018618, filed on Jun. 10, 2004.

(60) Provisional application No. 60/478,130, filed on Jun. 11, 2003.

(51) Int. Cl.
*A61F 2/28*    (2006.01)
*A61F 2/46*    (2006.01)
(Continued)

(52) U.S. Cl.
CPC .............. *A61F 2/28* (2013.01); *A61F 2/4644* (2013.01); *A61L 27/365* (2013.01); *A61L 27/3608* (2013.01); *A61L 27/3658* (2013.01); *A61L 27/38* (2013.01); *A61L 31/005* (2013.01); *A61F 2/4455* (2013.01); *A61F 2002/2817* (2013.01); *A61F 2002/2835* (2013.01); *A61F 2002/30059* (2013.01); *A61F 2002/30075* (2013.01); *A61F 2002/30153* (2013.01);
(Continued)

(58) Field of Classification Search
CPC .............................. A61F 2/28; A61L 2430/02
USPC ....................... 623/23.5, 23.51, 23.61–23.63
See application file for complete search history.

(56) References Cited

U.S. PATENT DOCUMENTS

| 159,334 A | 2/1875 | Kumpf |
|---|---|---|
| 781,882 A | 2/1905 | Hunter |

(Continued)

FOREIGN PATENT DOCUMENTS

| DE | 179 833 | 2/1905 |
|---|---|---|
| DE | 44 34 459 A1 | 4/1996 |

(Continued)

OTHER PUBLICATIONS

Abjornson et al., "A Novel Approach to Bone Grafting Substitutes", Society for Biomaterials, p. 1372 (2000).
(Continued)

*Primary Examiner* — Christopher D Prone
(74) *Attorney, Agent, or Firm* — Sorell Lenna & Schmidt LLP

(57) ABSTRACT

A method of repairing and/or treating bone is provided. The method includes implanting at a repair site an osteoimplant having a coherent aggregate of entangled elongate bone particles mixed with a biocompatible fluid carrier, the osteoimplant being flexible and further being formed as a strip at least one end of which possesses a tab for facilitating combination with another implant.

7 Claims, 3 Drawing Sheets

(51) Int. Cl.
   *A61L 27/36*      (2006.01)
   *A61L 27/38*      (2006.01)
   *A61L 31/00*      (2006.01)
   *A61F 2/44*       (2006.01)
   *A61F 2/30*       (2006.01)

(52) U.S. Cl.
   CPC ............... *A61F 2002/30329* (2013.01); *A61F 2002/30593* (2013.01); *A61F 2002/30677* (2013.01); *A61F 2002/30805* (2013.01); *A61F 2002/30957* (2013.01); *A61F 2002/30975* (2013.01); *A61F 2002/4649* (2013.01); *A61F 2210/0061* (2013.01); *A61F 2220/0025* (2013.01); *A61F 2230/0019* (2013.01); *A61F 2310/00293* (2013.01); *A61F 2310/00329* (2013.01); *A61F 2310/00365* (2013.01); *A61L 2430/02* (2013.01)

(56) References Cited

U.S. PATENT DOCUMENTS

| | | |
|---|---|---|
| 2,516,438 A | 7/1950 | Wheeler |
| 2,968,593 A | 1/1961 | Rapkin |
| 3,458,397 A | 7/1969 | Myers et al. |
| 3,609,867 A | 10/1971 | Hodosh |
| 3,739,773 A | 6/1973 | Schmitt et al. |
| 3,790,507 A | 2/1974 | Hodosh |
| 3,829,904 A | 8/1974 | Ling et al. |
| 3,891,997 A | 7/1975 | Herbert |
| 3,922,726 A | 12/1975 | Trentani et al. |
| 3,947,287 A | 3/1976 | Belde et al. |
| 4,059,684 A | 11/1977 | Gross et al. |
| 4,123,806 A | 11/1978 | Amstutz et al. |
| 4,134,792 A | 1/1979 | Boguslaski et al. |
| 4,172,128 A | 10/1979 | Thiele et al. |
| 4,191,747 A | 3/1980 | Scheicher |
| 4,209,434 A | 6/1980 | Wilson et al. |
| 4,224,698 A | 9/1980 | Hopson |
| 4,291,013 A | 9/1981 | Wahlig et al. |
| 4,294,753 A | 10/1981 | Urist |
| 4,355,331 A | 10/1982 | Georges et al. |
| 4,363,319 A | 12/1982 | Altshuler |
| 4,394,370 A | 7/1983 | Jefferies |
| 4,430,760 A | 2/1984 | Smestad |
| 4,440,370 A | 4/1984 | Rood |
| 4,440,750 A | 4/1984 | Glowacki et al. |
| 4,450,592 A | 5/1984 | Niederer et al. |
| 4,458,733 A | 7/1984 | Lyons |
| 4,472,840 A | 9/1984 | Jefferies |
| 4,485,097 A | 11/1984 | Bell |
| 4,512,038 A | 4/1985 | Alexander et al. |
| 4,516,276 A | 5/1985 | Mittelmeier et al. |
| 4,563,350 A | 1/1986 | Nathan et al. |
| 4,563,489 A | 1/1986 | Urist |
| 4,581,030 A | 4/1986 | Bruns et al. |
| 4,595,713 A | 6/1986 | St. John |
| 4,620,327 A | 11/1986 | Caplan et al. |
| 4,623,553 A | 11/1986 | Ries et al. |
| 4,627,853 A | 12/1986 | Campbell et al. |
| 4,627,931 A | 12/1986 | Malik |
| 4,636,526 A | 1/1987 | Dorman et al. |
| 4,678,470 A | 7/1987 | Nashef et al. |
| 4,698,375 A | 10/1987 | Dorman et al. |
| 4,709,703 A | 12/1987 | Lazarow et al. |
| 4,743,259 A | 5/1988 | Bolander et al. |
| 4,795,463 A | 1/1989 | Gerow |
| 4,795,467 A | 1/1989 | Piez et al. |
| 4,824,939 A | 4/1989 | Simpson |
| 4,842,604 A | 6/1989 | Dorman et al. |
| 4,857,269 A | 8/1989 | Wang et al. |
| 4,863,472 A | 9/1989 | Tormala et al. |
| 4,888,366 A | 12/1989 | Chu et al. |
| 4,902,296 A | 2/1990 | Bolander et al. |
| 4,919,939 A | 4/1990 | Baker et al. |
| 4,932,973 A | 6/1990 | Gendler |
| 4,946,792 A | 8/1990 | O'Leary |
| 4,950,296 A | 8/1990 | McIntyre |
| 4,961,707 A | 10/1990 | Magnusson et al. |
| 4,975,526 A | 12/1990 | Kuberasampath et al. |
| 4,994,030 A | 2/1991 | Glowczewskie, Jr. et al. |
| 5,001,169 A | 3/1991 | Nathan et al. |
| 5,007,930 A | 4/1991 | Dorman et al. |
| 5,015,247 A | 5/1991 | Michelson |
| 5,032,445 A | 7/1991 | Scantlebury et al. |
| 5,053,049 A | 10/1991 | Campbell et al. |
| 5,073,373 A | 12/1991 | O'Leary et al. |
| 5,092,887 A | 3/1992 | Gendler |
| 5,108,399 A | 4/1992 | Eitenmuller et al. |
| 5,112,354 A | 5/1992 | Sires |
| 5,123,925 A | 6/1992 | Smestad et al. |
| 5,139,527 A | 8/1992 | Redl et al. |
| 5,162,114 A | 11/1992 | Kuberasampath et al. |
| 5,171,278 A | 12/1992 | Pisharodi |
| 5,171,574 A | 12/1992 | Kuberasampath et al. |
| 5,197,882 A | 3/1993 | Jernberg |
| 5,207,710 A | 5/1993 | Chu et al. |
| 5,236,456 A | 8/1993 | O'Leary et al. |
| 5,284,655 A | 2/1994 | Bogdansky et al. |
| 5,290,558 A | 3/1994 | O'Leary et al. |
| 5,298,254 A | 3/1994 | Prewett et al. |
| 5,306,304 A | 4/1994 | Gendler |
| 5,314,476 A | 5/1994 | Prewett et al. |
| 5,314,478 A | 5/1994 | Oka et al. |
| 5,329,846 A | 7/1994 | Bonutti |
| 5,343,877 A | 9/1994 | Park |
| 5,366,507 A | 11/1994 | Sottosanti |
| 5,368,859 A | 11/1994 | Dunn et al. |
| 5,405,390 A | 4/1995 | O'Leary et al. |
| 5,405,402 A | 4/1995 | Dye et al. |
| 5,425,639 A | 6/1995 | Anders |
| 5,425,762 A | 6/1995 | Muller |
| 5,432,000 A | 7/1995 | Young et al. |
| 5,439,684 A | 8/1995 | Prewett et al. |
| 5,441,517 A | 8/1995 | Kensey et al. |
| 5,447,725 A | 9/1995 | Damani et al. |
| 5,449,375 A | 9/1995 | Vidal et al. |
| 5,455,041 A | 10/1995 | Genco et al. |
| 5,464,439 A | 11/1995 | Gendler |
| 5,476,880 A | 12/1995 | Cooke et al. |
| 5,480,436 A | 1/1996 | Bakker et al. |
| 5,484,601 A | 1/1996 | O'Leary et al. |
| 5,490,962 A | 2/1996 | Cima et al. |
| 5,496,375 A | 3/1996 | Sisk |
| 5,507,813 A | 4/1996 | Dowd et al. |
| 5,510,396 A | 4/1996 | Prewett et al. |
| 5,518,680 A | 5/1996 | Cima et al. |
| 5,531,791 A | 7/1996 | Wolfinbarger, Jr. |
| 5,545,222 A | 8/1996 | Bonutti |
| 5,556,430 A | 9/1996 | Gendler |
| 5,567,806 A | 10/1996 | Abdul-Malak et al. |
| 5,607,269 A | 3/1997 | Dowd et al. |
| 5,641,518 A | 6/1997 | Badylak et al. |
| 5,656,593 A | 8/1997 | Kuberasampath et al. |
| 5,662,710 A | 9/1997 | Bonutti |
| 5,676,146 A | 10/1997 | Scarborough |
| 5,683,459 A | 11/1997 | Brekke |
| 5,700,479 A | 12/1997 | Lundgren |
| 5,707,962 A | 1/1998 | Chen et al. |
| 5,723,117 A | 3/1998 | Nakai et al. |
| 5,727,945 A | 3/1998 | Dannenbaum |
| 5,782,919 A | 7/1998 | Zdeblick et al. |
| 5,807,437 A | 9/1998 | Sachs et al. |
| 5,846,484 A | 12/1998 | Scarborough et al. |
| 5,888,219 A | 3/1999 | Bonutti |
| 5,899,939 A | 5/1999 | Boyce et al. |
| 5,910,315 A | 6/1999 | Stevenson et al. |
| 5,922,753 A | 7/1999 | Petrie et al. |
| 6,025,538 A * | 2/2000 | Yaccarino, III ............ 128/898 |
| 6,030,635 A | 2/2000 | Gertzman et al. |
| 6,090,998 A | 7/2000 | Grooms et al. |
| 6,123,731 A | 9/2000 | Boyce et al. |
| 6,132,472 A | 10/2000 | Bonutti |
| 6,200,347 B1 * | 3/2001 | Anderson et al. ......... 623/16.11 |

(56) References Cited

U.S. PATENT DOCUMENTS

| | | | |
|---|---|---|---|
| 6,206,923 B1 | 3/2001 | Boyd et al. | |
| 6,224,630 B1 | 5/2001 | Bao et al. | |
| 6,294,187 B1* | 9/2001 | Boyce et al. | 424/422 |
| 6,311,690 B1 | 11/2001 | Jefferies | |
| 6,326,018 B1 | 12/2001 | Gertzman et al. | |
| 6,340,477 B1 | 1/2002 | Anderson | |
| 6,361,565 B1 | 3/2002 | Bonutti | |
| 6,375,663 B1 | 4/2002 | Ebner et al. | |
| 6,432,436 B1 | 8/2002 | Gertzman et al. | |
| 6,436,138 B1* | 8/2002 | Dowd et al. | 623/16.11 |
| 6,436,139 B1 | 8/2002 | Shapiro et al. | |
| 6,437,018 B1 | 8/2002 | Gertzman et al. | |
| 6,458,375 B1 | 10/2002 | Gertzman et al. | |
| 6,599,515 B1 | 7/2003 | Delmotte | |
| 6,599,520 B2 | 7/2003 | Scarborough et al. | |
| 6,616,698 B2 | 9/2003 | Scarborough | |
| 6,630,153 B2 | 10/2003 | Long et al. | |
| 6,632,247 B2 | 10/2003 | Boyer, II et al. | |
| 6,638,309 B2 | 10/2003 | Bonutti | |
| 6,652,592 B1 | 11/2003 | Grooms et al. | |
| 6,652,593 B2 | 11/2003 | Boyer, II et al. | |
| 6,706,067 B2 | 3/2004 | Shimp et al. | |
| RE38,522 E | 5/2004 | Gertzman et al. | |
| 6,733,534 B2 | 5/2004 | Sherman | |
| 6,736,853 B2 | 5/2004 | Bonutti | |
| 6,776,938 B2 | 8/2004 | Bonutti | |
| 6,808,585 B2 | 10/2004 | Boyce et al. | |
| 6,843,807 B1 | 1/2005 | Boyce et al. | |
| 6,855,167 B2 | 2/2005 | Shimp et al. | |
| 6,855,169 B2 | 2/2005 | Boyer, II et al. | |
| 6,863,694 B1 | 3/2005 | Boyce et al. | |
| 6,911,212 B2 | 6/2005 | Gertzman et al. | |
| 6,913,621 B2 | 7/2005 | Boyd et al. | |
| 7,045,141 B2 | 5/2006 | Merboth et al. | |
| 7,163,691 B2 | 1/2007 | Knaack et al. | |
| RE39,587 E | 4/2007 | Gertzman et al. | |
| 7,311,713 B2 | 12/2007 | Johnson et al. | |
| 7,323,193 B2 | 1/2008 | Morris et al. | |
| 2001/0020186 A1 | 9/2001 | Boyce | |
| 2002/0026244 A1 | 2/2002 | Trieu | |
| 2002/0029084 A1 | 3/2002 | Paul | |
| 2002/0035401 A1 | 3/2002 | Boyce et al. | |
| 2002/0055143 A1 | 5/2002 | Bell et al. | |
| 2002/0107570 A1 | 8/2002 | Sybert et al. | |
| 2002/0120338 A1 | 8/2002 | Boyer, II et al. | |
| 2002/0161449 A1 | 10/2002 | Muschler | |
| 2003/0009235 A1* | 1/2003 | Manrique et al. | 623/23.63 |
| 2003/0036800 A1 | 2/2003 | Meredith | |
| 2003/0045934 A1 | 3/2003 | Bonutti | |
| 2003/0093154 A1 | 5/2003 | Estes et al. | |
| 2003/0105528 A1 | 6/2003 | Shimp et al. | |
| 2003/0195629 A1 | 10/2003 | Pafford et al. | |
| 2004/0023387 A1 | 2/2004 | Morris et al. | |
| 2004/0097612 A1 | 5/2004 | Rosenberg et al. | |
| 2004/0220681 A1 | 11/2004 | Cole et al. | |
| 2005/0065214 A1 | 3/2005 | Kronenthal | |
| 2005/0170396 A1 | 8/2005 | Baker et al. | |
| 2006/0002976 A1 | 1/2006 | Kronenthal | |
| 2006/0013857 A1 | 1/2006 | Kronenthal | |
| 2006/0030948 A1 | 2/2006 | Manrique et al. | |
| 2006/0147545 A1 | 7/2006 | Scarborough et al. | |
| 2006/0280801 A1 | 12/2006 | Kronenthal | |

FOREIGN PATENT DOCUMENTS

| | | |
|---|---|---|
| DE | 29608321 U1 | 8/1996 |
| EP | 0 082 621 | 6/1983 |
| EP | 0 243 151 A2 | 10/1987 |
| EP | 0 267 015 | 5/1988 |
| EP | 0 321 442 A3 | 6/1989 |
| EP | 0 366 029 A3 | 5/1990 |
| EP | 0 406 856 | 1/1991 |
| EP | 0405429 A2 | 1/1991 |
| EP | 0 411 925 A2 | 2/1991 |
| EP | 0 413 492 A2 | 2/1991 |
| EP | 0 419 275 A1 | 3/1991 |
| EP | 0 483 944 A1 | 5/1992 |
| EP | 0 495 284 A1 | 7/1992 |
| EP | 0 520 237 | 12/1992 |
| EP | 0 555 807 A1 | 8/1993 |
| EP | 0 567 391 A1 | 10/1993 |
| EP | 0 693 523 A2 | 1/1996 |
| EP | 9506281 | 6/1997 |
| EP | 1142 581 A2 | 10/2001 |
| FR | 2691901 A1 | 12/1993 |
| GB | 2175807 A | 12/1986 |
| JP | 9059/1986 | 3/1986 |
| JP | 2121652 | 5/1990 |
| JP | 3210270 A | 9/1991 |
| JP | 4097747 A | 2/1992 |
| RU | 0880425 | 11/1981 |
| WO | WO 86/07265 | 12/1986 |
| WO | WO 89/04646 | 6/1989 |
| WO | WO 89/11880 | 12/1989 |
| WO | WO 94/21196 | 9/1994 |
| WO | WO 95/15776 | 6/1995 |
| WO | WO 96/39203 A1 | 12/1996 |
| WO | WO 97/25941 | 7/1997 |
| WO | WO 98/00183 A2 | 1/1998 |
| WO | WO 98/17209 A2 | 4/1998 |
| WO | WO 98/40113 | 9/1998 |
| WO | WO 99/39757 A1 | 8/1999 |
| WO | WO 00/34556 | 6/2000 |
| WO | WO 00/35510 | 6/2000 |
| WO | WO 00/50102 | 8/2000 |
| WO | WO 01/06584 A1 | 2/2001 |
| WO | WO 02/02156 A2 | 1/2002 |
| WO | WO 02/47587 A | 6/2002 |
| WO | WO 2004/108023 A1 | 12/2004 |
| WO | WO 2006/057011 A2 | 6/2006 |
| WO | WO 2006/076712 A2 | 7/2006 |

OTHER PUBLICATIONS

Bolander et al., "The Use of Demineralized Bone Matrix in the Repair of Segmental Defects", The Journal of Bone and Joint Surgery, vol. 68-A, No. 8, pp. 1264-1274 (1986).

Bostrom et al., "Use of Bone Morphogenic Protein-2 in the Rabbit Ulnar Nonunion Model", Clinical Orthopaedics and Related Research, No. 327, pp. 272-282 (1996).

Edwards et al., "Osteoinduction of Human Demineralized Bone: Characterization in a Rat Model", Clinical Orthopaedics & Ref. Res. 357:219-228, Dec. 1998.

Gekko et al., "Mechanism of Protein Stabilization by Glycerol: Preferential Hydration in Glycerol-Water Mixtures", vol. 20, No. 16, pp. 4667-5676 (1981).

Gepstein et al., "Bridging large Defects in Bone by Demineralized Bone Matrix in the Form of a Powder", The Journal of Bone and Joint Surgery, vol. 69-A, No. 7, pp. 984-991, 1987.

Glowacki et al., "Demineralized Bone Implants", Symposium on Horizons in Plastic Surgery, vol. 12, No. 2, pp. 233-241, 1985.

Glowacki et al., "Fate of Mineralized and Demineralized Osseous Implants in Cranial Defects", Clacified Tissue Int. 33: 71-76, 1981.

Groeneveld et al., "Mineralized Processes in Demineralized Bone Matrix Grafts in Human Maxillary Sinus Floor Elevation", John Wiley & Sons, Inc. pp. 393-402 (1999).

Kaban et al., "Treatment of Jaw Defects with Demineralized Bone Implants", Journal of Oral and Maxillofacial Surgery, pp. 623-626 (Jun. 6, 1998).

Kakiuchi et al., "Human Bone Matrix Gelatin as a Clinical Alloimplant", International Orthopaedics, 9, pp. 181-188 (1985).

Kubler, et al., "Allogenic bone and Cartilage Morphogenesis", J. Craniomaxillofac. Surg. 19(7): 238-288, 1991.

Lewandrowski, et al., "Kinetics of Cortical Bone Demineralization:controlled demineralization—a new method for modifying cortical bone allografts," J. Biomed. Mater. Res. 31:365-372, 1996.

McLaughlin, et al., "Enhancements of Bone Ingrowth by the Use of Bone Matrix as a Biologic Cement", Clinical Orthopaedics and Related Research, No. 183, pp. 255-261 (Mar. 1984).

(56) References Cited

OTHER PUBLICATIONS

Mellonig, "Decalicified Freeze-Dried Bone Allograft as an Implant Material in Human Periodontal Defects", The International Journal of Periodontics and Restorative Dentistry, pp. 41-45, 1984.
Mulliken, J.B. and Glowacki, "Induced Osteogenesis for Repair and Construction in the Craniofacial Region", J. Plastic and Reconstructive Surgery, May 1980, p. 553-559.
Neigal, et al., "Use of Demineralized Bone Implants in Orbital and Craniofacial", Opthal. Plast. Reconstrs. Surg., 12: 108-120, 1996.
Paralkar, et al., PNAS, 100(11): 6736-6740, 2003.
Perez, B.J., et al., "Mechanical properties of a discontinous random fiber composite for totally bioabsorbable fracture fixation devices", Paper presented in: Bioengineering Conference, 1995 Proceedings of the 1995 IEEE 21st Annual Northeast, May 22-23, 1995, pp. 55-56.
Ray, Robert, et al., "Bone Implants: Preliminary Report of an Experimental Study", Journal of Bone and Joint Surgery, vol. 29A (5), Oct. 1957.
Russell, et al., Orthopaedics, 22(5):524-53, May 1, 1999.
The Term "Substantially", Merriam-Webster Online Dictionary, at the web—http://www.m-w.com, p. 1, (Website Confirmed by examiner on Nov. 27, 2013).
Todescan, et al., "A Small Animal Model for Investigating Endosseous Dental Implants: Effect of Graft Materials on Healing of Endoss, Porous-Surfaced Implants Placed in a Fresh Extraction Socket", The Journal of Oral and Maxillofacial Implants, vol. 2, No. 2, pp. 217-223, 1987.
Ueland, et al., "Increased Cortical Bone Content of Insulin-Like Growth Factors in Acromegalic Patients", J. Clin. Endocrinol. Metab., 84(1): 123-127, 1999.
Urist, M.R., et al., "The Bone Induction Principle", Clin. Orthop. Rel. Res. 53:243-283, 1967.
Urist, M.R., "Bone Formation by Autoinduction", Science, 150(698):893-9, 1965.
Whiteman, et al., J. Hand. Surg. 188:487, 1993.
Whittaker, et al., "Matrix Metalloproteinases and Their Inhibitors—Current Status and Future Challenges", Celltransmissions, 17(1):3-14, 2003.
Xiaobo, et al., Orthop., No. 293, pp. 360-365, 1993.
Zhang, et al., "A Quantative Assessment of Osteoinductivity of Human Demineralized Bone Matrix", J. Periodontal. 68(11): 1076-1084, 1997.
Gher, Marlin E. et al., "Bone Grafting and Guided Bone Regeneration for Immediate Dental Implants in Humans", J. Periodontology, 1994, 65:881-891.
Product literature for Gore Resolut XT, Bioabasorbable membrane from Gore Regenerative Technologies, Palm Beach Gardens, FL, 1998.
Product literature for Bio-Gide®, Resorbable barrier membrane from OsteoHealth Co., Division of Luitpold Pharmaceutical, Inc., 1998.
Mellonig, James T. D.D.S., M.S., "Bone Allografts in Periodontal Therapy", Clinical Orthopaedics and Related Research, No. 324, Mar. 1996.
Thitiwan, Teparat, et al., "Clinical Comparison of Bioabsorbable Barriers With Non-Resorbable Barriers in Guided Tissue Regeneration in the Treatment of Human Intrabony Defects", J. Periodontolov, Jun. 1998.
Block, Michael S., D.M.D., et al., "Bone Maintenance 5 to 10 years After Sinus Grafting", J. Oral Maxillofacial Surg., vol. 56, pp. 706-714, 1998.
Parma-Benfenati, S., et al., "Histologic Evaluation of New Attachment Utilizing a Titanium-Reinforced Barrier Membrane in a Mucogingival Recession Defect. A Case Report", J. Periodontologv, Jul. 1998.
Bobyn et al., "The Optimum Pore Size for the Fixation of Porous-Surfaced Metal Implants by Ingrowth of Bone", Clinical Orthopaedics and Related Research, 1980, pp. 263-270.
Jurgensen, K., M.D., et al., "A New Biological Glue for Cartilage-Cartilage Interfaces: Tissue Transglutaminase", Journal of Bone and Joint Surgery, Inc., Feb. 1997, pp. 185-193.

Lewandrowski, et al., "Flexural Rigidity in partially Demineralized Diaphyseal Bone Grafts", Clinical Orthopaedics and Related Research, No. 317, 1995, pp. 254-262.
Lewandrowski, et al., "Kinetics of cortical bone demineralization: Controlled demineralization—a new method for modifying cortical bone allografts", Journal of Biomedical Materials Research, vol. 31, 1996, pp. 365-372.
Takayasu, Ito, M.D., et al., "Sensitivity of Osteoinductive Activity of Demineralized and Defatted Rat Femur to Temperature and Furation of Heating", Clinical Orthopaedics and Related Research, No. 316, 1995, pp. 267-275.
Meijer, et al., "Radiographic Evaluation of Mandibular Augmentation with Prefabricated Hydroxylapatite/Fibrin Glue Implants", Journal of Oral and Maxillofacial Surgery, 1997, pp. 138-145.
Stevenson, et al., "Factors Affecting Bone Graft Incorporation", Clinical Orthopaedics and Related Research, No. 323, 1996, pp. 66-74.
Glowacki, et al., "Application of the Biological Principle of Induced Osteogenesis for Craniofacial Defects", The Lancet, 1981, vol. 1, No. 8227, pp. 959-962.
Kiviranta, et al., "The Rate of Calcium Extraction During EDTA Decalcification from Thin Bone Slices as Assessed with Atomic Absorption Spectrophotometry", Histochemistrv 68, 1980, pp. 119-127.
Covey, et al., "Clinical Induction of Bone Repair With Demineralized Bone Matrix or a Bone Morphogenetic Protein", Orthopaedic Review, Aug. 1989, vol. XVIII, No. 8, pp. 857-863.
Habal, et al., "Autologous Corticocancellous Bone Paste for Long Bone Discontinuity Defects: An Experimental Approach", Annals of Plastic Surgery, Aug. 1985, vol. 15, No. 2, pp. 138-142.
Crowe, et al., "Inhibition of Enzymatic Digestion of Amylose by Free Fatty Acids in Vitro Contributes to Resistant Starch Formation", J. Nutr., 2000, vol. 130, No. 8, pp. 2006-2008.
Reddi, et al., Proc. Natl. Acad. Sci, 69, 1972, pp. 1601-1605.
Stairs, Robert A., "Calculation of surface tension of salt solutions: effective polarizability of solvated ions." Can. J. Chern. 73: pp. 781-787 (1995).
Abel, E., "The vapor phase above the system sulfuric acid-water." J. Phys. Chern. 50(3), pp. 260-283 (1946).
Urist, et al. "Bone Formation in Implants of Partially and Wholly Demineralized Bone Matrix," Clinical Orthopaedics and Related Research, vol. 71, pp. 271-278 (1970).
Grafton™ Allogenic Bone Matrix (ABM), Advertising Brochure, Advanced Processing of Human Allograft Bone, Osteotech, Inc., 1992.
Frenkel, et al. "Use of Demineralized Bone Matrix Gel to Enhance Spine Fusion", 19th Annual Meeting of the Society for Biomaterials, Apr. 28-May 2, 1993, Birmingham, AL, p. 162.
Stevenson, et al. "Long Bone Delect Healing Induced by a New Formulation of Rat Demineralized Bone Matrix Gel," $40^{th}$ Annual Meeting, Orthopedic Research Society, Feb. 21-24, 1994, New Orleans, LA, p. 205-35.
Ruppert, Rainer, et al. "Human bone morphogenetic protein 2 contains a heparin-binding site which modifies its biological activity," Eur. J. Biochem, 237(1): 295-302 (1996).
Kubler, N.R., et al. "EHBMP-2: The first BMP-variant with osteoinductive properties," Mund Kiefer Gesichtschir, 3(1): S134-S139 (1999).
Reddi, A. Hari, "Interplay between bone morphogenetic proteins and cognate binding proteins in bone cartilage development: noggin, chordin and DAN," Arthritis Research, 3(1): 1-5 (2001).
Gazzerro, Elisabetta, et al. "Bone Morphogenetic Proteins Induce the Expression of Noggin, Which Limits Their Activity in Cultured Rat Osteoblasts," Jour. of Clin. Invest., 102(12): 2106-2114 (1998).
Yamaguchi, Akira, "Recent advances in researchers on bone formation—Role of BMP in bone formation," Nihon Rinsyo, 56(6): 1406-1411 (1998).
Dallas, Sarah L., et al., "Dual Role for the Latent Transforming Growth Factor-β Binding Protein in Storage of Latent TGF-β in the Extracellular Matrix and as a Structural Matrix Protein," Jour. of Cell Biol., 131(2): 539-549 (1995).

(56) References Cited

OTHER PUBLICATIONS

Pedrozo, Hugo A., et al. "Vitamin $D_3$ Metabolites Regulate LTBP1 and Latent TGF-β1 Expression and Latent TGF-β1 Incorporation in the Extracellular Matrix of Chohdrocytes," Jour. of Cell. Biochem., 72(1): 151-165 (1999).

Pedrozo, Hugo A., et al. "Growth Plate Chondrocytes Store Latent Transforming Growth Factor (TGF)-β1 in Their Matrix Through Latent TGF-β1 Binding Protein-1," Jour. of Cellular Physiology, 177(2): 343-354 (1997).

Bautista, Catalino M., et al. "Isolation of a novel insulin-like growth factor (IGF) binding protein from human bone: A potential candidate for fixing IGF-II in human bone," Biochem. and Biophys. Research Communications, 176(2): 756-763 (Apr. 30, 1991).

Mohan, S., "Insulin-Like Growth Factor Binding Proteins in Bone Cell Regulation," Growth Regulation, 3(1): 67-70 (1993).

Jada, vol. 133, Dec. 2002. http://jada.ada.org/cgi/reprint/133/12/1610-a.

* cited by examiner

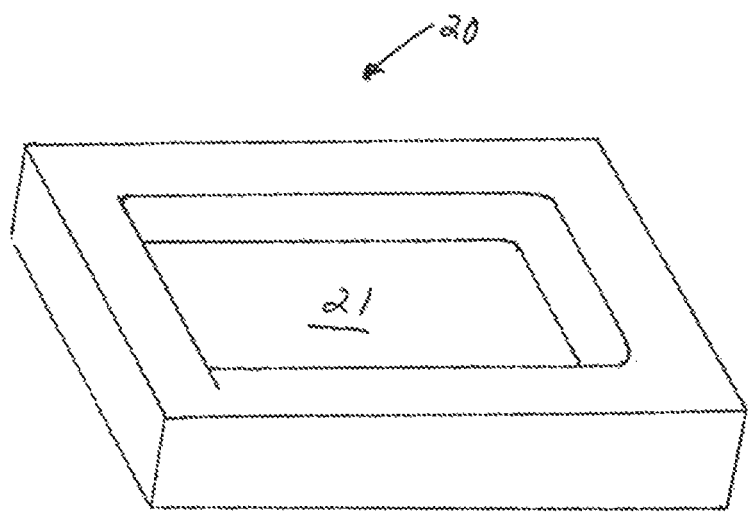
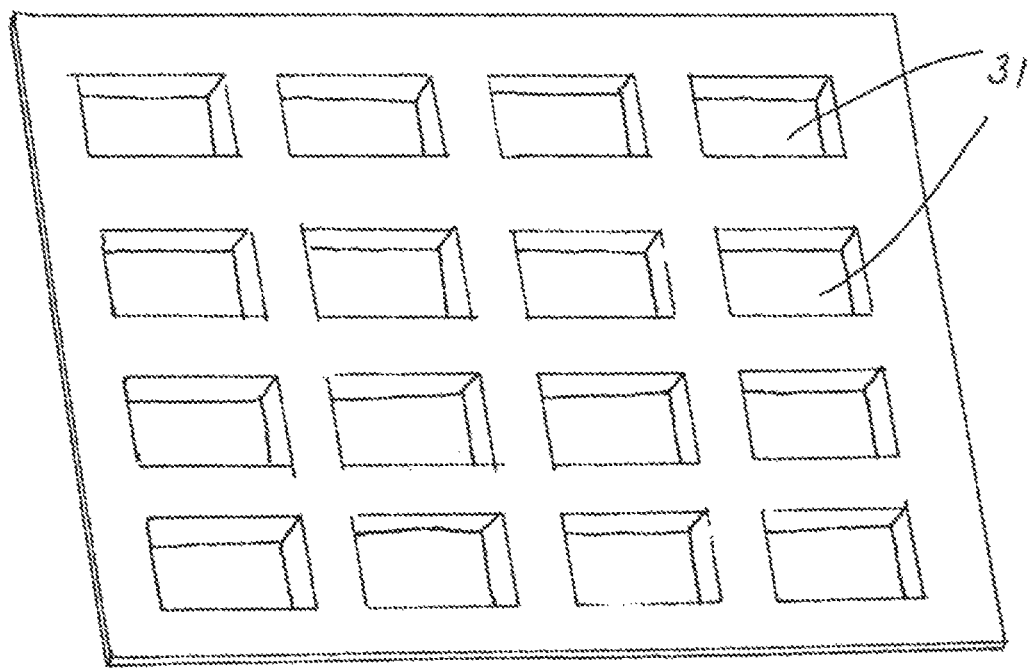

OSTEOIMPLANTS AND METHODS FOR THEIR MANUFACTURE

CROSS-REFERENCE TO RELATED APPLICATION

This application is a continuation of U.S. patent application Ser. No. 11/489,262, filed Jul. 19, 2006, now U.S. Pat. No. 8,268,008, which is a continuation of U.S. patent application Ser. No. 11/297,735, filed Dec. 8, 2005, now abandoned, which is a continuation of PCT/US2004/018618 filed Jun. 10, 2004, which claims the benefit of provisional U.S. patent application Ser. No. 60/478,130, filed Jun. 11, 2003, the entire contents of which are incorporated by reference herein.

BACKGROUND OF THE INVENTION

1. Field of the Invention

This invention relates to bone-derived implant, or osteoimplants, made up of a coherent aggregate of elongate bone particles and to methods for their manufacture. Among their many applications, the osteoimplants herein can be fashioned in various configurations and for use in repairing bone defects, e.g., as strips for use in spinal fusion procedures, as trough-shaped implants especially useful for PostLateral Fusion ("PLF") procedures, and as putty-like materials that can be molded on site and packed between fragments of bone fractures, between bony projections and into large cavities.

2. Description of the Related Art

Bone-derived implants have been used extensively to treat various medical problems in human and animal orthopedic surgical practice. The use of such implants has also extended to the fields of, e.g., cosmetic and reconstructive surgery, dental reconstructive surgery, podiatry, orthopaedics, neurosurgery and other medical fields involving hard tissue. The use of autograft bone (where the patient provides the source), allograft bone (where another individual of the same species provides the source) or xenograft bone (where another individual of a different species provides the source) is well known in both human and veterinary medicine. In particular, transplanted bone is known to provide support, promote healing, fill bony cavities, separate bony elements (such as vertebral bodies), promote fusion (where bones are induced to grow together into a single, solid unit) or stabilize the sites of fractures. More recently, processed bone has been developed into shapes for use in new surgical applications or as new materials for implants that were historically based on non-biologically derived materials.

Osteoconductive materials are ones that guide bone growth but do not stimulate it. Examples are bone chips and ceramics. Osteoinductive materials actually cause bone to form and result in faster and more certain healing. Examples of osteoinductive materials include cancellous bone, demineralized bone and various growth factors. The most common source of osteoinductive material is the patient's own bone. Typically, in spinal surgery, this is harvested from the iliac crest in the form of bone chips and marrow. While effective, it causes secondary damage (to the harvest site) and requires preparation before it can be used. Furthermore, it is somewhat difficult to maintain in place due to its semi-fluid nature.

Demineralized bone is an alternative to bone chips and marrow as an osteoinductive material. Compositions containing demineralized bone come in various forms including gels, pastes, fibers, sheets, and the like. The more fluid compositions such as those made with bone powder am relatively easy to implant at the repair site but difficult to maintain in place. Osteoimplants made with elongate bone particles, in contrast to those made from bone powder, are better able to maintain their implanted shape and mass and to resist or delay erosion by body fluids and irrigation liquids. Elongate bone particles and methods for their manufacture are described in, inter alia, U.S. Pat. Nos. 5,314,476, 5,507,813, 5,607,249 and 6,436138, in pending U.S. patent application Ser. No. 10/137,862, filed May 2, 2002 and WO 03/082159.

SUMMARY OF THE INVENTION

It is an object of the invention to provide osteoimplants derived from elongate bone particles.

It is as particular object of the invention to provide an osteoimplant of predetermined shape and dimensions made up of a coherent aggregate of elongate bone particles.

It is another particular object of the invention to provide is low density osteoimplant which possesses an open pore structure allowing the osteoimplant to readily absorb fluids such as blood and yet still retain its original shape.

It is another object of the invention to provide an osteoimplant fabricated from elongate bone particles which is flexible when water has been removed and which can be implanted while in the dry state.

It is yet another object of the invention to provide methods for making osteoimplants in possessing the aforementioned characteristics.

It is still another object of the invention to provide methods of treating bone defects which utilize osteoimplants possessing the aforementioned characteristics.

Other specific objects of the invention include the provision of an osteoimplant in the form of a strip and the use of the strip, e.g., in a spinal fusion procedure such as one to treat scoliosis.

Yet another specific object of the invention is the provision, of an osteoimplant in the form of a putty-like material which can be readily molded by the surgeon during a surgical procedure so as to conform to a bone repair site.

Still another specific object of the invention is the provision of a method for making a trough-shaped osteoimplant.

The term "osteoimplant" as utilized herein is intended to refer to any device or material for implantation that aids or augments bone formation or healing. Osteoimplants are often applied at a bone defect site, e.g., one resulting from injury, defect brought about during the course of surgery, infection, malignancy or developmental malformation. The osteoimplants herein may be suitably sized and shaped as required for use in any of a wide variety of orthopedic, neurosurgical and oral and maxillofacial surgical procedures such as the repair of simple and compound fractures and non-unions, external and internal fixations, joint constructions such as arthrodesis, general arthroplasty, deficit filling, discectomy, laminectomy, anterior cervical and thoracic operations, spinal fusions, etc. Therefore, the osteoimplants herein are intended for implantation at a bony site and are made of any biocompatible material(s), e.g., bone or bone particles, biocompatible synthetic materials, combinations thereof, etc, and may be designed for either animal or human use. Specifically, the osteoimplant suitable for use according to the disclosure herein will be any osteoimplant without limitation to the particular material(s) the osteoimplant is made of or the size or shape of the cavity.

The term "biocompatible" and expressions of like import shall be understood to mean the absence of stimulation of an undesired biological response to an implant and is distinguished from a mild, transient inflammation and/or granulation response which can accompany implantation of most foreign objects into a living organism and is also associated with the normal healing response. Materials useful to the invention herein shall be biocompatible if, at the time of implantation, they are present in a sufficiently small concentration such that the above-defined condition is achieved.

The term "particle" as utilized herein is intended to include bone pieces of all shapes, sizes, thickness and configuration such as fibers, threads, narrow strips, thin sheets, chips, shards, powders, etc., that posses regular, irregular or random geometries. It should be understood that some variation in dimension will occur in the production of the particles of this invention and particles demonstrating such variability in dimensions are within the scope in this invention. Particles useful herein can be homogenous, heterogeneous, and can include mixtures of human, xenogenic and/or transgenic material.

The term "human" as utilized herein in reference to suitable sources of implantable materials refers to autograft bone which is taken from at least one site in the graftee and implanted in another site of the graftee as well as allograft bone which is bone taken from a donor other than the graftee.

The term "autograft" as utilized herein refers to tissue that is extracted from the in ended recipient of the implant.

The term "allograft" as utilized herein refers to tissue intended for implantation that is taken from a different member of the same species as the intended recipient.

The term "xenogenic" as utilized herein refers to material intended for implantation obtained from a donor source of a different species than the intended recipient. For example, when the implant is intended for use in an animal such as a horse (equine), xenogenic tissue of, e.g., bovine, porcine, caprine, etc., origin may be suitable.

The term "transgenic" as utilized herein refers to tissue intended for implantation that is obtained from an organism that has been genetically modified to contain within its genome certain genetic sequences obtained from the genome of a different species. The different species is usually the same species as the intended implant recipient but such limitation is merely included by way of example and is not intended to limit the disclosure here anyway whatsoever.

The expressions "whole bone" and "substantially fully mineralized bone" refer to bone containing its full or substantially full, original mineral content.

The expression "demineralized bone" includes bone that has been partially, fully, segmentally or superficially (surface) demineralized.

The expression "substantially fully demineralized bone" as utilized herein refers to bone containing less than about 8% of its original mineral context.

The term "osteogenic" as applied to the bone plug and/or elongate bone particle composition thereof shall be understood as referring to the ability of an osteoimplant to facilitate or accelerate the growth of new bone tissue by one or more mechanisms such as osteogenesis, osteoconduction and/or osteoinduction.

The term "osteoinduction" shall be understood to refer to the mechanism by which a substance recruits cells from the host that have the potential for forming new bone and repairing bone tissue. Most osteoinductive materials can stimulate the formation of ectopic bone in soft tissue.

The term "osteoconduction" shall be understood to refer to the mechanism by which a non substance serves as a suitable template or substrate along which bone may grow.

The term "osteogenesis" shall be understood to refer to cell-mediated bone formation.

The term "device" as utilized herein is intended to refer to any osteoimplant that is manufactured predominately of non-bone materials. Such devices are typically made of those materials commonly used m the manufacture of biocompatible implants, e.g., biocompatible metals such as surgical Bioglass®, biocompatible polymeric materials, e.g., polylactic acid, polytetrafluoroethylene, etc., or any other suitable biocompatible non-bone material.

The term "shaped" as applied to the aggregate of elongate bone particles herein refers to a determined or regular form or configuration in contrast to an indeterminate or vague form or configuration (as in the case of a lump or other solid matrix of no special form) and is characteristic of such materials as sheets, plates, disks, cones, pins, screws, tubes, teeth, bones, portion of bone, wedges, cylinders, threaded cylinders, and the like, as well as more complex geometric configurations.

The term "coherent" as applied to the aggregate of elongate bone particles refers to the ability of the bone particles to adhere to each other either, e.g., by entanglement, or by the use of a biocompatible binder or adhesive.

The expression "three-dimensional" refers to the ability of the coherent aggregate of elongate bone particles to assume any desired shape and size.

The expression "open pore structure" as it applies to the coherent aggregate of elongate bone particles constituting one embodiment of osteoimplant herein shall be understood as referring to the low density, absorbent, sponge-like nature of the osteoimplant in which there are a plurality of accessible pores or openings which are present throughout the entire volume of the aggregate.

The term "incorporation" utilized herein refers to the biological mechanism whereby host tissue gradually replaces the osteoimplant of the invention with native host bone tissue. This phenomenon is also known in the scientific literature as "bone remodeling" or "cellular based remodeling" and "wound healing response". Therefore, the term "incorporation" utilized herein shall be understood as embracing what is conveyed to those skilled in the art by the foregoing expressions.

The expression "further treatment" as utilized herein refers to procedures such as, e.g., lyophilizing, cross-linking treatment, re-mineralization, sterilization, etc., performed either before, during or after the step of making, the osteoimplant as well as post-processing procedures such as, machining, laser etching, welding, assembling of parts, cutting, milling, reactive etching, etc.

Another particularly useful embodiment of the invention herein is an osteoimplant provided as a coherent aggregate, or matrix of elongate bone particles possessing an open pore structure and a low bulk density. The open pore structure of the aggregate renders the osteoimplant highly absorbent of surrounding liquids. The osteoimplant formed from the aggregate is flexible when dry (e.g., when containing less than about 6 weight percent water) and does not require time-consuming rehydration prior to implantation, it can assume any desired shape and/or configuration and can be cut to the desired dimensions, e.g., with surgical scissors, before and/or after the aggregate has absorbed fluid. Even art the wetted/hydrated state, the osteoimplant will maintain its original shape and coherency and can be readily handled by the medical practitioner.

Osteoinductivity can be conveniently quantified as the amount of bone formed in an ectopic site in an athymic made rat. Scores are rated 0 to 4. The osteoimplants of the invention exhibit osteoinductivities of at least about 2, typically at least about 3, when measured in an athymic rat assay as described in Edwards J T, Diegmann M H, Scarborough N L, Osteoinduction of Human Demineralized Bone: Characterization in an Animal Model, Clin. Orthop. Rel. Res. 357:219 228 (1998):

The osteoimplant of the invention can be combined with a wide variety of biocompatible substances which can be introduced into the porous matrix of the osteoimplant and/or into large cavities, depressions, and the like, produced in the osteoimplant. Thus, the implant herein functions as a highly effective carrier and/or delivery vehicle for bone-growth inducing and/or otherwise medically useful substances.

Further provided is a method of fabricating the osteoimplant herein which comprises providing a quantity of elongate demineralized bone particles, mixing the elongate demineralized bone particles with at aqueous wetting agent to provide a fluid composition preferably containing from about 5 to about 40 volume percent swollen, hydrated bone particles, placing the liquid composition in a mold, and removing a sufficient amount of aqueous wetting agent, e.g., by heating the fluid composition in the substantial absence of pressure at elevated temperature, to provide an osteoimplant comprising a shaped, coherent aggregate, or matrix, of elongate bone particles, preferably one of open pore structure and possessing a low bulk density, e.g., of less than about 3.0 g/cm$^3$, preferably less than about 2.5 g/cm$^3$ and more preferably less than about 1.5 g/cm$^3$.

Further provided in accordance with the invention is a method of repairing and/or treating bone comprising implanting at a bone repair site an osteoimplant which comprises a shaped and dimensioned coherent aggregate of elongate bone particles, preferably one of open pore structure and possessing a low bulk density, e.g., on the order of less than about 3.0 g/cm$^3$, preferably less than about 2.5 g/cm$^3$ and more preferably less than about 1.5 g/cm$^3$.

The osteoimplant of the invention can be readily applied to virtually any bone repair site in the body and can be utilized alone or in combination with one or more adjunct medical devices and/or procedures. The osteoimplant of the invention finds particular utility in the areas of dental reconstructive surgery and spinal fusion where substantial amounts of body fluid, e.g., saliva and/or blood, are frequently encountered or where autograft (e.g., local bone, marrow or iliac crest, etc.) is incorporated in the osteoimplant. The unique ability of the osteoimplant to absorb body fluids and still retain its original shape represents as significant advance in the medical field. Additionally, the absorbent nature of the bioimplant encourages the wicking up and recruitment of cells which are essential to osteogenesis.

BRIEF DESCRIPTION OF THE SEVERAL VIEWS OF THE DRAWINGS

FIG. 4 illustrates a trough-shaped osteoimplant manufactured by the method of the invention; and, FIGS. 5-7 illustrate a molding surface, perforated cassette and lid that can be used in manufacturing the trough-shaped osteoimplant of FIG. 4.

DESCRIPTION OF THE PREFERRED EMBODIMENTS

Figure 1:
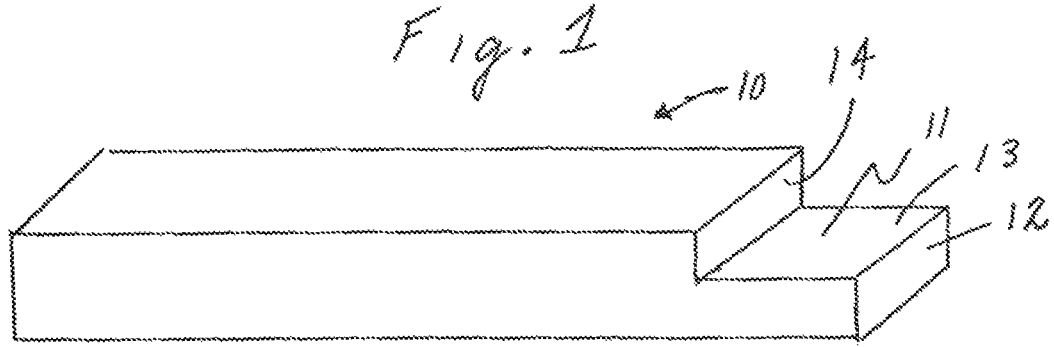
FIG. 1 illustrates an osteoimplant of this invention in the form of a strip especially adapted for use in is spinal fusion procedure such as scoliosis.

The composition of the osteoimplant herein can be made up of from about 5 to about 100 weight percent fully demineralized and/or demineralized elongate bone particles. At least about 50 weight percent, preferably at least about 60 weight percent, and more preferably at least about 90 weight percent of the bone particles present in the osteoimplant herein are of the elongate variety. Any non-elongate bone particles that are optionally included in the osteoimplant can possess a wide range of dimensions, e.g., powders, chips, etc. The elongate bone particles form a coherent aggregate, or matrix, which imparts porosity and absorbency to the osteoimplant.

The bone component of the osteoimplant can be obtained from cortical, cancellous, and/or corticocancellous allogenic, xenogenic or transgenic bone tissue. In general, allogenic bone tissue is preferred as the source of the bone component. The bone component can be fully mineralized or partially or fully demineralized. Porcine and bovine bones are particularly advantageous types of xenogenic bone tissue that can be used individually or in combination as source for the bone particles although of course other xenogenic or transgenic bone tissues can also be used. Combinations of fully mineralized and demineralized bone can also be used.

The bone particles employed in the fabrication of the osteoimplant of this invention are generally characterized as "elongate", they possess relatively high median length to median thickness ratios. In overall appearance, the elongate bone particles can be described as filaments, fibers, threads, slender or narrow strips, etc. Thus, e.g., the elongate bone particles can possess a median length of from about 0.05 to about 400 mm, preferably from about 1 to about 100 mm, a median width of from about 0.05 to about 2 mm, preferably from about 0.08 to about 1.5 mm and a ratio of median length to median width of from about 10:1 to about 2000:1 preferably of from about 20:1 to about 600:1. If desired, the elongate bone particles can be graded into different sues to reduce eliminate any less desirable size(s) of particles that may be present.

The elongate bone particles can be readily obtained by any one of several methods, e.g., by milling or shaving the surface of an entire bone or relatively large section of bone. Employing a milling technique, one can obtain a mass of elongate bone particles containing at least about 20 weight percent of bone particles coming within at least one of the aforesaid ranges of dimensions.

Another procedure for obtaining the elongate bone particles herein, particularly useful for pieces or sections of bone of up to about 100 mm in length, is the bone processing mill described in commonly assigned U.S. Pat. No. 5,407,269. Use of this bone mill results in the production of long, thin strips which quickly curl lengthwise to provide tubular-like elongate bone particles. These elongate bone particles may then optionally be ground, fractured, shredded or fragmented to yield smaller particles. This may be achieved using a grating device, a mortar and pestle or other conventional procedures for shredding and grating materials. The elongate bone particles and or shredded fragments are optionally subjected to demineralization in accordance with known and conventional procedures in order to reduce their inorganic mineral content. Such demineralization can occur prior to or after forming the elongate particles. Demineralization methods remove the inorganic mineral component of bone by employing acid solutions. Such methods are well known in the art, see for example, Reddi et al., *Proc. Nat. Acad. Sci.* 69, pp 1601-1605 (1972), incorporated herein by reference. The strength of the acid solution, the shape of the bone particles and the duration of the demineralization treatment will determine the extent of demineralization. Reference m this regard may be made to Lewandrowski et al., *J. Biomed Materials Res.* 31, pp. 365-372 (1996), also incorporated herein by reference.

As used herein, the expression "superficially demineralized" refers to bone particles which have undergone surface demineralization as a result of which they possess one or more regions of surface-exposed collagen. The expression "partially demineralized bone" refers to bone possessing less than its original mineral content but not less than about weight percent of its original mineral content. As previously stated, "substantially fully demineralized bone" refers to bone containing less than about 8 weight percent, and usually less than about 3 weight percent, of its original mineral content. Mixtures of one or more of the foregoing types of demineralized bone particles can be employed. Moreover, one or more of the foregoing types of demineralized bone particles can be employed in combination with nondemineralized bone particles, i.e., bone particles that have not been subjected to demineralization. It will be understood by those skilled in the art that fully demineralized bone particles yield a more porous mass compared to whole bone or superficially demineralized bone particles.

When prepared in whole or in part from bone particles that are only superficially demineralized or nondemineralized, the osteoimplant will tend to possess a fairly high compression strength, e.g., one approaching that of natural bone. Accordingly, when an osteoimplant exhibiting rigidity, e.g., a compression strength of on the order of from about 5 to about 200 MPa, preferably from about 20 to about 100 MPa and more preferably from about 25 to about 75 MPa, is desired, superficially demineralized bone particles and/or nondemineralized bone particles are advantageously employed.

In a preferred demineralization procedure, relatively large mineralized bone piece(s) from which demineralized bone particles are subsequently obtained, or fully mineralized bone particles obtained from such relatively large mineralized bone piece(s), are subjected to a defatting/disinfecting step, which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing microorganisms and viruses. Ordinarily, at least about 10 to about 40 percent by weight of water (i.e., about 60 to about 90 weight percent of defatting agent such as alcohol) should be present in the defatting disinfecting solution to produce optimal lipid removal and disinfecting within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. Acids which can be employed in this step include inorganic acids such as hydrochloric acid and organic acids such as peracetic acid. After acid treatment, the demineralized bone particles are rinsed with sterile water for injection to remove residual amounts of acid and thereby raise the pH. The elongate bone particles used in the manufacture of the plug naturally entangles or may be mechanically entangled employing e.g., the wet laying procedure, skin to a paper-making process, described in aforementioned U.S. Pat. No. 5,507,813 to Dowd et al., to provide a sheet-like coherent mass of bone particles which can thereafter be shaped, e.g., by cutting, molding etc., before or after drying and/or other processing into configurations corresponding to those desired for the bone plug of this invention.

If desired, the bone particles before or after their being gathered into a coherent aggregate can be modified in one or more ways, e.g., their protein content can be augmented or modified as described in U.S. Pat. Nos. 4,743,259 and 4,902,296, the contents of which are incorporated by reference herein. The elongate bone particles can also be admixed with one or more substances such as binders/fillers, plasticizers, biostatic/biocidal agents, surface active agents, drugs, DNA vectors and the like, prior to, during, or after shaping the elongate bone particles into a desired configuration and size. One or more of such substances can be combined with the bone particles by soaking or immersing the elongate bone particles in a solution or dispersion of the desired substance, by physically admixing the elongate bone particles and the desired substance, co-extrusion of the substance and particles, and the like.

Suitable binders/fillers include cyanoacrylates, epoxy-based compounds, dental resin sealants, dental resin cements, calcium phosphate sand calcium sulfate self-setting cements, glass ionomer cements, polymethyl methacrylate, gelatin-resorcinol-formaldehyde glues, protein and collagen-based glues, acrylic resins, cellulosics, bioabsorbable polymers such as polyglycolide, polylactide, glycolide-lactide copolymers, polycaprolactone, polyanhydrides, polycarbonates, polyorthoesters, polyamino acids, polyarylates, polycyanoacrylates, polyhydroxybutyrate, polyhydroxyvalyrate, polyphosphazenes, and polyvinylpyrrolidone, carbohydrate polymers, polyiminocarbonates, polypropylene fumarates, polyanhydride esters, polytetrafluorethylene, hexacryl, Hyaluronic acid, fibrin, fibrin-collagen, polyethylene, glycol, glues, mucopolysaccharides, mussel adhesive proteins, fatty acids and fatty acid derivatives, etc.

Other suitable biners/fillers include bone powder, demineralized bone powder, porous calcium phosphate ceramics, hydroxyapatite, tricalcium phosphate, Bioglass® and other calcium phosphate materials, calcium sulfate or calcium carbonate particles, etc.

Suitable plasticizers include liquid polyhydroxy compounds such as glycerol, monoacetin, diacetin, hydrogels, etc.

Suitable biostatic/biocidal agents include antibiotics, povidone, sugars, mucoplysaccharides, etc.

Suitable surface-active agents include the biocompatible nonionic, cationic, anionic and amphoteric surfactants. It will be understood by those skilled in the art that the foregoing list is not intended to be exhaustive and that other materials may be admixed with bone particles within the practice of the disclosure herein such as disclosed in U.S. Pat. No. 5,073,373, the contents of which are incorporated by reference herein.

Any of a variety of bioactive substances can be incorporated in, or associated with, the bone particles before, during or after fabrication of the osteoimplant. Thus, one or more of such substances can be combined with the elongate bone particles by soaking or immersing them in a solution or dispersion of the desired substance(s). Bioactive substances include physiologically or pharmacologically active substances that act locally or systemically in the host.

Representative classes of bioactive factors which can be readily combined with the bone particles include, trophic factors, analgesics, anti-cancer agents, vaccines, adjuvants, antibodies, neuroleptics, genes and genetic elements for transfection including viral vectors for gene therapy, cells or cellular components, etc. A list of more specific examples would therefore include, collagen, insoluble collagen derivatives, etc, and soluble solids and/or liquids dissolved therein, e.g., antiviricides, particularly those effective against HIV and hepatitis; antimicrobials and/or antibiotics such as erythromycin, bacitracin, neomycin, penicillin, polymicin B, tetracyclines, biomycin, chloromycetin, and streptomycins, cephalosporins, ampicillin, azactam, tobramycin, clindamycin and gentamicin, etc.; biocidal/biostatic sugars such as dextran, glucose, etc.; amino acids, peptides, vitamins, inorganic elements, co-factors for protein synthesis; hormones; endocrine tissue or tissue fragments, synthesizers, enzymes such as collagenase, peptidases, oxidases, etc., polymer cell scaffolds with parenchymal cells, angiogenic drugs and polymeric carriers containing such drugs; collagen lattices; antigenic agents; cytoskeletal agents; cartilage fragments, modified living cells such as chondrocytes, bone marrow cells, mesenchymal stem cells, natural extracts, genetically engineered living cells or otherwise modified living cells, DNA delivered by plasmid or viral vectors, genes or genetic elements, tissue transplants, demineralized bone powder, autogenous tissues such as blood, serum, soft tissue, bone marrow, etc.; bioadhesives; non-collagenous proteins: such as osteopontin, osteonectin, bone sialo protein, laminin, fibrinogen, vitronectin, thrombospondin, proteoglycans, decorin, beta glycan, biglycan, aggrecan, versican, tenascin, matrix gla protein, hyaluronan, amino acids, amino acid residues, peptides, bone morphogenic proteins (BMPs); osteoinductive factor (OIF); fibronectin (FN); endothelial cell growth factor (ECGF); cementum attachment extracts (CAE); ketanserin; human growth hormone (HGH); animal growth hormones; epidermal growth factor (EGF); interleukin-1 (IL-1) human alpha thrombin; transforming growth factor (TGF-beta); insulin-like growth factor (IGF-1) (IGF-2); platelet derived growth factors (PDGF); fibroblast growth factors (FGF, aFGF, bFGF, etc.); periodontal ligament chemotactic factor (PDLGF); somatotropin; bone digestors; antitumor agents; immuno-suppressants; fatty acids (including polar and non-polar fatty acids); permeation enhancers, e.g., fatty acid esters such as laureate, myristate and stearate monoesters of polyethylene glycol, enamine derivatives, alpha-keto-aldehydes, etc.; and nucleic acids; inorganic elements, inorganic compounds, cofactors for protein synthesis, hormones, soluble and insoluble components of the immune system; soluble and insoluble receptors including truncated forms; soluble, insoluble and cell surface bound ligands including truncated forms; chemokines, bioactive compounds that are endocytosed; endocrine tissue or tissue fragments, growth factor binding proteins, e.g., insulin-like growth factor binding protein (IGFBP-2) (IGFBP-4) (IGFBP-5) (IGFBP-6); angiogenic agents, bone promoters, cytokines, interleukins, genetic material, genes encoding bone promoting actions, cells containing genes encoding bone promoting action; growth hormones such as somatotrophin, bone digestors; antitumor agents; cellular attractants and attachment agents; immuno suppressants; bone resorption inhibitors and stimulators; angiogenic and mitogenic factors; bioactive factors that inhibit and stimulate secondary messenger molecules; cell adhesion molecules, e.g., cell-matrix and cell-cell adhesion molecules; secondary messengers, monoclonal antibodies specific to cell surface determinants on mesenchymal stem cells, clotting factors; externally expanded autograft or xenograft cells, nucleic acids and any combination thereof. The amounts and types of such optionally added substances can vary widely with optimum levels and combinations being readily determined in a specific case by routine experimentation.

Various shapes of osteoimplant can be made by using extrusion or injection molding techniques, compression molds, pre-formed molds in which the material can be placed to obtain its final shape, or pre-formed shapes which can be used to cut desired shape from pre-formed material. Further to this, devices can be used that allow introduction of various agents in to the molding devices or treatments of the molds to assist in the forming of various shapes, such as, but not limited to, cross linking agents or beat or cooling, of the molds and/or during the forming process. Employing such procedures, various sizes and shapes of osteoimplant can be provided such as those illustrated in FIGS. 1a-h.

In one embodiment herein, an osteoimplant as previously described is made by forming demineralized elongate bone particles into a coherent aggregate and thereafter either cutting the osteoimplant from the aggregate or, preferably, to reduce waste, molding the aggregate into an osteoimplant of the desired size and configuration. To fabricate the coherent mass of elongate bone particles, a quantity of elongate bone particles with or without one or more optional materials is mixed with a suitable biocompatible fluid component, e.g., water, organic protein solvent, physiological saline, concentrated saline solution, ionic solution of any kind, aqueous sugar solution, liquid polyhydroxy compound such as glycerol or glycerol ester, hydrogel, etc., or mixtures thereof. The suitable biocompatible fluid can optionally contain one or more substances such as binder, filler, plasticizer, biostatic/biocidal agent, surface active agent, bioactive substance, etc., as previously described to form a slurry or paste. Excess fluid is then removed from the slurry or paste, e.g., by applying the slurry or paste to a mesh or screen and draining away excess fluid. Functionally, the biocompatible fluid provides a coherent aggregate of elongate bone particles whose consistency can be described as shape-sustaining but readily deformable, e.g., putty-like.

If desired, the elongate bone particles can be dried, e.g., at from about 30° to about 80° C. and preferably from about 40° to about 50° C., for from about 1 to about 3 hours, and then lyophilized under conditions that are well known in the art, e.g., at a shelf temperature of from about −20° to about −35° C., a vacuum of from about 150 to about 100 mTorr and for a period of time ranging from about 4 to about 48 hours. The drying and lyophilization steps will result in the production of a coherent mass of entangled elongate bone particles that is relatively strong when dry and flexible when wetted or hydrated.

In another embodiment of the general method described above, the coherent aggregate of elongate bone particles can be subjected to a compressive force, e.g., of up to about 100,000 psi, during and/or after the step of removing excess liquid and/or while the drained-but-still-wet bone particles are being dried. If desired, the compressed coherent mass can be as lyophilized to provide an especially strong and rigid mass.

In yet as further embodiment disclosed herein, the elongate bone particles, in combination with bone particles possessing other geometries such as mineralized and demineralized bone powders and pieces, can be combined with a wetting agent as described above to produce a flowable composition containing front about 5 to about 100%, preferably from about 20 to about 60%, volume percent of one particles of all types, the remainder of the composition comprising wetting agent. The wetting agent can optionally comprise one or more biocompatible components as previously described. The wetting agent will cause the demineralized elongate boric particles to swell and increase in flexibility. The fluid composition will possess a consistency ranging from a slurry or paste to wet dough, depending on the amount of wetting agent used. The critical aspect is that the elongate bone particles be suspended in and evenly distributed throughout the fluid composition. This is to be contrasted with the "wet laying" procedure of U.S. Pat. No. 5,507,813 in which wetting agent is substantially removed to produce a dense mat of bone particles.

In this embodiment, the fluid composition is formed by mixing the bone particles and wetting agent to form a liquid slurry, stirring the shiny for a suitable period of time sufficient to allow the wetting agent to penetrate the demineralized elongate bone particles, and removing enough wetting agent, e.g., by draining through a sieve, sufficient to provide a fluid composition containing from about 5 to about 25, preferably front about 10 to about 15, volume percent bone particles. Substantial mechanical entanglement of the elongate bone particles will occur. Suitable wetting agents include biocompatible liquids and/or hydrogels such as previously described. Optionally, the wetting agent can comprise dissolved or admixed therein one or more biocompatible substances such as previously described.

Preferred wetting agents for forming the wetted mass of bone particles include water, liquid polyhydroxy compounds and their esters, and polyhydroxy compounds in combination with water and/or surface-active agents. Specific polyhydroxy compounds of the foregoing type include glycerol and its monoesters and diesters derived from low molecular weight carboxylic acids, e.g., monoacetin and diacetin (respectively, glycerol monoacetate and glycerol diacetate), ethylene glycol, diethylene glycol, triethylene glycol, 1,2-propanediol, trimethylolethane, trimethylolpropane, pentaerythritol, sorbitol, polyethylene glycol, polyoxyalkylenes, e.g., Pluronics®, and the like. The preferred polyhydroxy compounds possess up to about 12 carbon atoms and, where their esters are concerned, are preferably the monoesters and diesters. Of these, glycerol is especially preferred as it improves the handling characteristics of the bone particles wetted therewith and is biocompatible and easily metabolized. Most preferred are solutions of polyhydroxy compounds in water, with glycerol/water solutions in weight ratios ranging from about 40:60 to about 5:95, respectively, being especially preferred. Mixtures of polyhydroxy compounds or esters, sorbitol dissolved in glycerol, glycerol combined with monoacetin and/or diacetin, etc., are also useful.

Where the bone particles have a tendency to quickly or prematurely separate or to otherwise settle out from the fluid composition such that formation of a homogeneous suspension of bone particles in wetting agent is rendered difficult, it can be advantageous to include within the composition a suspension aid. Thus. e.g., where the wetting agent is water and/or glycerol and separation of bone particles occurs to an excessive extent where a particular application is concerned, a thickener such as a solution of polyvinyl alcohol, polyvinylpyrrolidone, cellulosic ester such as hydroxypropyl methylcellulose, carboxy methylcellulose, pectin, xanthan gum, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend particles, etc., can be combined with the wetting agent in an amount sufficient to significantly improve the suspension-keeping characteristics oldie composition. Furthermore, suspension aids that generate gas bubbles inside the fluid composition can be employed. The gas bubbles reduce the tendency of the bone particles to settle out and include peroxides and bicarbonate.

As stated previously, the fluid composition is preferably placed in a mold which optionally is configured and dimensioned at least partially in the shape of the final osteoimplant. Care must be taken to ensure that minimal, if any, pressure is applied to the composition m the mold which would effect compaction of the elongate bone particles. This is in contrast to the wet-lay procedure described in U.S. Pat. No. 5,507,813.

The composition is then dried at a temperature of from about 30° C. to about 80° C., preferably from about 30° C. to about 40° C. to effect removal of water and provide a shaped material. Following the drying step, the shaped material is dried e.g., freeze-dried, employing a shelf temperature of from about −20° to about −35° C. and a vacuum of from about 150 to about 100 mTorr applied for from about 4 to about 48 hours. The resulting shaped material is porous and absorbent and maintains its shape and cohesiveness upon absorption of fluid. The implant can be easily cut with scissors or other cutting tools in either the dry or rehydrated state.

Alternatively, a slurry of demineralized elongate bone particles can be injected into a porous tube. The bone particles can be dried and lyophilized in the tube, then removed and cut to length. Examples of suitable porous tubes are dialysis tubing, sausage casings, and rigid metal or plastic tubing perforated with a series of small holes (the holes generally being small enough that a few fibers escape, preferably 0.2 mm or less). It is also possible to use rigid tubing with large holes, and line with another tube that will contain the bone particle slurry such as a flexible dialysis tube. The slurry can be injected into the tube by any suitable means, for example a disposable plastic syringe or a slurry pump. If a thin, flexible tube is used to form the osteoimplant, the osteoimplant can be cut to length (after drying) while inside the tube by cutting through both the tube and the material inside. Alternatively, the dried aggregate elongate bone particles can be removed from the flexible tube (preferably by cutting the tube away) or from a rigid tube (preferably by pushing the material out of the tube) and then cut. Cutting is facilitated by using a cutting jig or guide similar to a cigar cutter or a small double bladed guillotine type of device where the blade spacing equals the desired plug length. Osteoimplants that are dried in a porous tube can have a tougher skin on their outer circumferential surface due to more rapid water loss from the surface than the interior. This can be advantageous in that the osteoimplant will resist insertion and handling forces better. The thickness and toughness of the skin can be influenced by a combination of drying conditions and tubing, porosity.

Optionally, the exposed collagen on the surfaces of mutually contacting bone particles in the osteoimplant can be chemically linked to each other employing techniques such as those disclosed in U.S. Pat. No. 6,294,187, a copy of which is included herewith and is to be regarded as an integral part of this provisional application. These crosslinking procedures result in the formation of chemical bonds between the surface-exposed collagen of mutually contacting surface-demineralized and/or substantially completely demineralized elongate bone particles making up, or contained in, the aggregate of naturally or mechanically entangled elongate bone particles.

Where a mold is employed to shape the coherent mass of bone particles into the osteoimplant of this invention, the walls of the mold can be coated with a slurry or paste containing partially and/or fully demineralized bone particles followed by addition of a slurry or paste containing non-demineralized and/or superficially demineralized bone particles (or vice versa. The resulting molded osteoimplant contains at least one region, e.g., an outer surface, composed of partially and/or fully demineralized bone particles and at least one region, e.g., a core, composed of non-demineralized and/or superficially demineralized bone particles. In this manner, the differential in compressive strength, porosity, osteogenicity and other properties between partially and/or fully demineralized bone particles on the one hand and non-demineralized and/or superficially demineralized bone particles on the other hand can be exploited. For example, where the osteoimplant is employed in a load-bearing situation, non-demineralized anchor superficially demineralized bone particles can be concentrated in that region of the osteoimplant which will be subjected to an applied load at the implant site.

The osteoimplants of the invention can vary widely in density, e.g., from about 0.1 g/cm³ to about 10 g/cm³. Low densities, those not exceeding about 3.0 g/cm³, are preferred. More preferred are densities of from about 0.5 to about 2.0 g/cm³ and most preferred are those of from about 0.8 to about 1.2 g/cm³.

The density (and void volume) of the osteoimplant can be controlled by the amount (usually described in grams) of bone fibers which are molded within a given mold volume. Practically speaking, using additional fibers to produce a higher density osteoimplant within a specified volume mold, will require the application of more pressure. In addition, if excess liquid is not removed prior to pressurization, the extrusion of more liquid must be accommodated when molding at higher pressures. One preferred embodiment of the invention features a fixed rectangular mold (mold body) fitted with a cover (mold lid) having a closely fitting lid with a protruding surface extending into the mold. When the mold lid is applied, the protruding surface inserts into the mold body and serves as the upper interior surface of the mold. With the lid in place the interior volume of the mold is defined (and the ultimate volume of the bioimplant). The height of the mold body will be designed to accommodate the required volume of demineralized bone fibers to be molded. The depth of the protruding surface of the lid is designed to produce the desired interior volume after application and pressurization. Alternately, ridges or other protrusions may be placed in the mold body to create tabs, lips, flanges or other reverse shapes in the final bioimplant.

A specific density osteoimplant is then prepared as follows: following demineralization, the elongated bone particles are suspended in shiny form with aqueous medium. A sample of the slurry is vacuum filtered to remove free residual liquid, and then lyophilized. The weight of wet slurry giving rise to the lyophilized weight is then determined. This conversion is used to determine the wet weight of bone particles required to produce the desired density osteoimplant in the given mold volume. The appropriate amount of bone particles are placed in the mold body and a gentle vacuum is applied to remove residual free solution. The lid is then applied and pressurized molding is performed in the presence of the appropriate amount of heat for the designated amount of time. Following demolding the osteoimplant is lyophilized.

Typically, the lyophilized osteoimplant of this invention, including its putty-like moldable forms, will possess a residual moisture (water) content of from about 0.6 to about 6.0 weight percent. This residual moisture, in combination with other non-volatile biocompatible materials, such as liquids, permits the lyophilized osteoimplant such as the strip of FIG. 1 to form the constructs or combinations shown in FIGS. 2 and 3 by slight pressure, e.g., finger pressure applied to the superimposed tabs.

The foregoing description and embodiments were chosen and described to best explain the principles of the invention and its practical applications thereby enabling others skilled in the act to best utilize the invention in its various embodiments and with various modifications as are suited to the particular use contemplated. Therefore, the foregoing descriptions of the preferred embodiments of the disclosure herein have been presented for purposes of illustration and description and are not intended to be exhaustive or to limit the invention to the precise forms disclosed. Obviously, many other modifications and variations are possible in light of the above teachings.

The following examples illustrate the practice of the present invention and in no way limit the scope of the claims appended hereto.

Example 1

Figure 2:
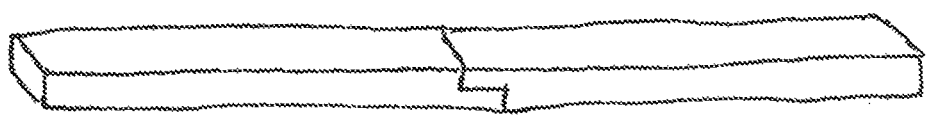
FIGS. 2 and 3 illustrate various combinations of the strips of FIG. 1.
Figure 3:
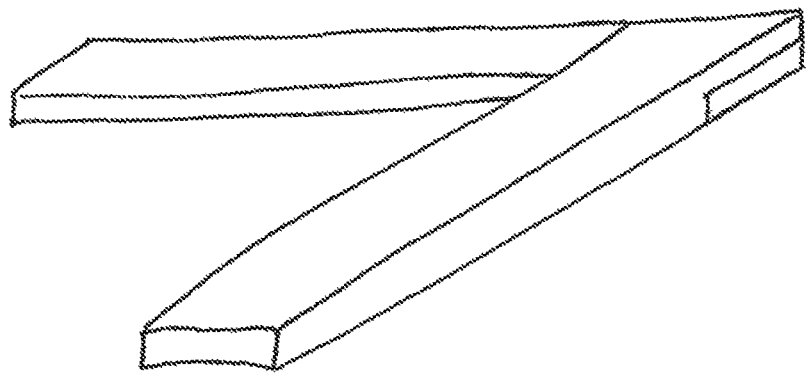

This example illustrates the preparation of an osteoimplant of the invention in the form of the generally rectangular strip shown in FIG. 1. Osteoimplant 10 possesses a tab 11 of step-like configuration which facilitates combining like strips as shown in FIGS. 2 and 3. Tab 11 includes a first face 12, a flat surface 13 and a second face 14. In general, the osteoimplant can possess a length (inclusive of tab 11) of from about 2 cm to about 50 cm and preferably from about 5 cm to about 20 cm, a width of from about 0.2 cm to about 5 cm, and preferably from about 0.5 cm to about 3 cm, and a depth of from about 0.2 cm to about 2.0 cm, and preferably from about 0.5 cm to about 1.0 cm, with a ratio of length to width of from about 1 to about 5, preferably from about 1 to about 10 and most preferably from about 1 to about 20. Specific dimensions of osteoimplant 10 are a length (inclusive of tab 11) of 10 cm or 20 em, a width of 1.0 cm, a height of 0.8 cm, a height of 0.4 cm for each of faces 12 and 14 and a length of 1 cm, for flat surface 13.

Osteoimplant 10 is initially formed as a single sheet with a predetermined thicknesses, e.g., of about 0.4 cm to about 1.2 cm which, following lyophilization, is cut into strips of the desired configuration and dimensions. The sheet is prepared by uniformly combining from about 250 g to about 350 g of elongate demineralized bone particles with from about 250 ml to about 1750 ml of glycerol and from about 250 ml to about 3500 ml of distilled deionized water to provide a slurry. The volume of glycerol added per 1 gram of bone particle may vary from about 1 ml to about 5 ml of glycerol per gram of bone. The volume of water added per 1 gram of bone particles may vary from about 1 ml to about 10 ml per grain of bone. The elongate bone particles possess a median length of about 1 to about 100 mm, a median width of about 0.08 to about 1.5 mm and a ratio of median length to median width of about 20:1 to about 600:1. The slurry is then introduced into a rectangular cassette (mold) possessing two raised ridges on one or two sides so as to provide the tab feature following the cutting of the resulting sheet into strips. The raised ridge(s) can be from about 0.2 cm to about 1.0 cm, preferably 0.3 cm to about 0.6 cm in height and from about 0.2 cm to about 5.0 cm, preferably from about 0.5 cm to about 2.0 cm, in width. After a period of from about 1 to 8 hours to permit swelling and hydration of the bone particles, the sheet is lyophilized under conventional lyophilization conditions, cut into individual strips and aseptically packaged for storage and/or shipment. In one preferred embodiment the density of the strips based on their dimensions and weight is calculated to be about 0.952 g/cm³ to about 0.966 g/cm³.

Because of their tab feature, several strips can be attached to, an interlocked with, each other as shown in FIGS. 2 and 3 while maintaining the same depth dimension. The strips may b sutured together, glued, cemented, clipped, pinned, screwed or otherwise fastened to each other to form a virtually any desired length. The length of the strip permits the surgeon to lay it close to the spinous processes of the spine and in the gutters of the spine in a long, continuous and cohesive manner. The strip can also be wrapped around any or all of the posterior elements to permit spinal fusion. This is advantageous because the instrumentation (metal bars, screws and hooks, etc) attached to vertebrae during many spinal fusion procedures are not osteoinductive or osteoconductive. The strip herein provides the osteogenicity, osteoinductivity and osteoconductivity to encourage fusion of the spinous processes, superior articular processes, transverse processes, mamillary processes (essentially all posterior elements of the spine), etc. The strip can be used in PostLateral Fusion procedures in smaller patients or in any indication where distances between vertebrae are smaller. Because of its dimensions, the strip can easily be implanted between screws or hooks and the vertebral bodies to encourage spinal fusion.

Example 2

This example illustrates the preparation of a putty-like, easily moldable osteoimplant composition in accordance with the invention.

Approximately 200 g to about 300 g of the elongate bone particles used in making the strip-configured osteoimplant of Example 1 are uniformly combined with from about 5 ml to about 15 ml of glycerol per gram of elongate bone particles and from about 5 mls to about 20 ml of distilled deionized water per grant of elongate bone particles to form a slurry which is permitted to swell and hydrate over a period of from 1 to 8 hours. Optionally, prior to either the addition of glycerol, water or both, the elongate fibers may be grated or shredded to reduce any one or more of their overall dimensions. A further optional treatment would be to knead blend, grind or shred the elongate fibers after the addition of glycerol, water or both. Excess liquid is drained from the slurry and the mixture is thereafter lyophilized under conventional lyophilization conditions. The resulting putty-like osteoimplant material is aseptically packaged for storage and/or shipment.

Example 3

This example illustrates the manufacture of the trough-like osteoimplant 20 shown in FIG. 4. Osteoimplant 20 possesses a generically rectangular shape and features a trough-like rectangular depression 21. A quantity of such osteoimplants can be conveniently formed using form 30 shown in FIG. 5, cassette 40 shown in FIG. 6 and lid 50 shown in FIG. 7.

Figures 6, 7:
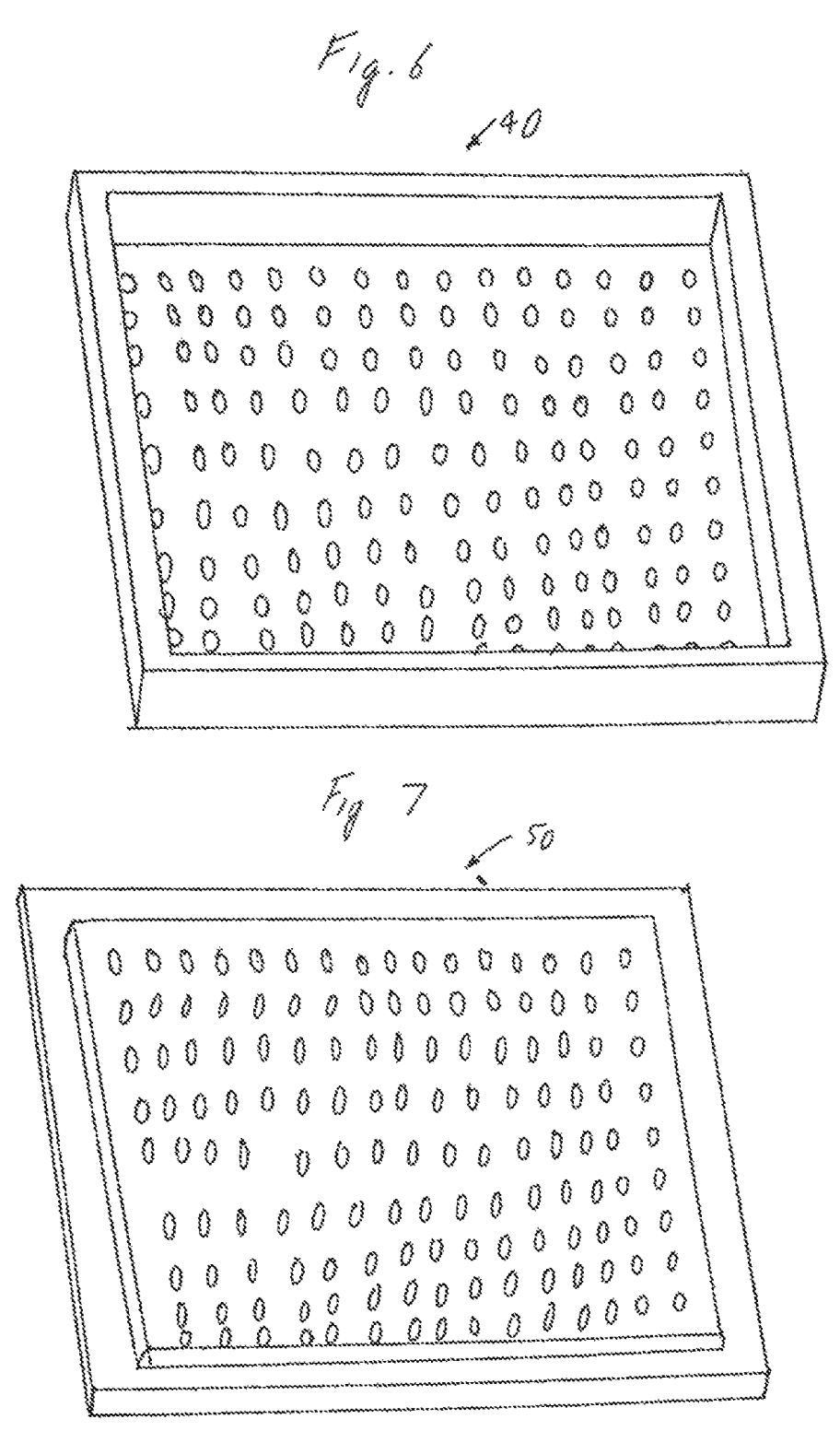

A shiny of swollen, hydrated demineralized elongated bone particles in glycerol and water prepared as described in Example 2 is introduced into cassette 40 of FIG. 6. The perforated base of the cassette permits excess liquid to drain from the slurry. A molding surface in the form of sheet 30 of FIG. 5 having little or no adherency for the slurry and possessing depressions 31 is than impressed upon the exposed surface of the slurry with the application of a gentle amount of pressure so as to provide a molded sheet of substantially uniform thickness (from about 0.5 cm to about 1.0 cm) possessing depressions conforming to the depressions in the molding surface. One suitable molding surface that can be used herein with generally good results is a thermoformed clear polypropylene sheet possessing the desired number, shape and site of depressions 31. With sheet 30 in place, lid 50 of FIG. 7 is placed on top of the cassette-sheet assembly. Lid 58 can be non-perforated or, if desired, perforated as shown.

The cassette-sheet-lid assembly containing molded, drained slurry is then heated at about 35 to about 50° C. for about 4 to about 6 hours after which the molded material is lyophilized as in Example 1, lid 50 and sheet 30 are removed, the molded material is removed from the cassette and cut into individual though-shaped implants 20 as shown in FIG. 4. The individual implants are then aseptically packaged for storage and/or shipment.

What is claimed:

1. A method of repairing and/or treating bone comprising removing water from an osteoimplant to bring the osteoimplant to a dry state via drying the osteoimplant at a temperature of about 40° C. to about 50° C. for a period of time of about 1 to about 3 hours; implanting the osteoimplant at a repair site, the osteoimplant comprising a coherent aggregate of entangled elongate bone particles mixed with a biocompatible fluid carrier and wrapping the osteoimplant around a posterior element of a vertebra to permit spinal fusion, the osteoimplant having at least one region comprising demineralized bone particles and at least one region comprising non-demineralized bone particles, the osteoimplant being flexible when water has been removed and is implanted while in the dry state without being rehydrated prior to implantation, the osteoimplant further being formed as a strip at least one end of which possesses a tab for facilitating combination with another implant, the osteoimplant having a residual moisture of from about 0.6 to about 6.0 weight percent and a bulk density of 0.8 to about 1.2 g/cm$^3$.

2. The method of claim 1 wherein the osteoimplant is used in a spinal fusion procedure.

3. The method of claim 2 wherein the spinal fusion procedure is a scoliosis procedure.

4. The method of claim 1, wherein the elongate bone particles comprise at least about 90 weight percent of bone particles present in the osteoimplant.

5. The method of claim 1, wherein the tab has a step-like configuration.

6. The method of claim 5, wherein the tab comprises a first flat surface defining a longitudinal axis, a first face extending from the first flat surface in a first direction transverse to the longitudinal axis, a second flat surface extending transverse to the first face and parallel with the longitudinal axis, a second face extending from the second flat surface in the first direction.

7. The method of claim 5, wherein the osteoimplant extends between said at least one end and a second oppositely positioned end along a longitudinal axis and the tab extends from said at least one end along the longitudinal axis.

* * * * *